(12) United States Patent
Avshalom et al.

(10) Patent No.: US 10,349,769 B2
(45) Date of Patent: Jul. 16, 2019

(54) AUTOMATIC APPARATUS FOR PUTTING STERILE GLOVES ON HANDS

(71) Applicants: Shimon Avshalom, Bet Shemesh (IL); Yomtov Sardeheli, Bet Shemesh (IL)

(72) Inventors: Shimon Avshalom, Bet Shemesh (IL); Yomtov Sardeheli, Bet Shemesh (IL)

( * ) Notice: Subject to any disclaimer, the term of this patent is extended or adjusted under 35 U.S.C. 154(b) by 65 days.

(21) Appl. No.: 15/569,397

(22) PCT Filed: Apr. 25, 2016

(86) PCT No.: PCT/IL2016/050437
§ 371 (c)(1),
(2) Date: Oct. 26, 2017

(87) PCT Pub. No.: WO2016/174672
PCT Pub. Date: Nov. 3, 2016

(65) Prior Publication Data
US 2018/0289190 A1    Oct. 11, 2018

(30) Foreign Application Priority Data
Apr. 26, 2015   (IL) ........................................... 238458

(51) Int. Cl.
*A47G 25/90*       (2006.01)
*A61B 42/50*       (2016.01)

(52) U.S. Cl.
CPC ............ *A47G 25/904* (2013.01); *A61B 42/50* (2016.02)

(58) Field of Classification Search
CPC ......... A61B 42/50; A61B 42/40; A61B 42/10; A61B 42/00; A47G 25/904
See application file for complete search history.

(56) References Cited

U.S. PATENT DOCUMENTS

| | | | | |
|---|---|---|---|---|
| 3,695,493 A * | 10/1972 | Karr | ..................... | A47G 25/904 2/162 |
| 4,889,266 A * | 12/1989 | Wight | .................... | A61B 42/50 223/111 |
| 4,915,272 A * | 4/1990 | Vlock | .................. | A47G 25/904 206/278 |
| 6,832,708 B2 * | 12/2004 | Sinai | ..................... | A47G 25/904 223/111 |
| 6,932,253 B2 * | 8/2005 | Sato | ....................... | A47G 25/904 223/111 |
| 10,143,528 B2 * | 12/2018 | Gaines | ................... | A47G 25/90 |
| 10,143,529 B2 * | 12/2018 | Gaines | ................... | A61B 42/60 |
| 2004/0149788 A1 | 8/2004 | Sato | | |

FOREIGN PATENT DOCUMENTS

JP          2002224139 A *   8/2002   ............. A61B 19/04

* cited by examiner

*Primary Examiner* — Michael C McCullough

(57) ABSTRACT

A gloving apparatus that comprises a glove box, a glove-lifting device, a glove-opening device, and a glove-inflating device. The glove box is designed to contain gloves. The glove-lifting device is designed to lift gloves, one at a time, from the glove box and insert the glove opening over said glove-opening device. The glove-lifting device comprises a vertical rod with one or more fastening devices at the bottom end, and vertical and horizontal activators. The glove-opening device has four spreading fingers, each of which can move horizontally and vertically using activators. The glove-inflating device comprises a sealing ring, an air tubule, and an activator that can move the sealing ring back and forth.

2 Claims, 27 Drawing Sheets

AUTOMATIC APPARATUS FOR PUTTING STERILE GLOVES ON HANDS

TECHNICAL FIELD

The present invention refers to an automatic apparatus for putting sterile gloves on hands, or in other words, a gloving apparatus.

BACKGROUND ART

It is customary, and sometimes necessary, to use sterile gloves in operating theaters, laboratories, and in various other places in which a sterile environment must be maintained. The user, for instance a surgeon preparing for surgery, usually scrubs and disinfects his or her hands with soap and a disinfectant and then puts on a pair of sterile gloves. While putting the gloves on his or her hands, the user touches the gloves, potentially contaminating the exterior of the gloves. Touching the exterior of the gloves, even after scrubbing and disinfecting, may contaminate them with bacteria. The present invention describes a system that offers a solution to this problem.

LIST OF DRAWINGS

The intention of the drawings attached to the application is not to limit the scope of the invention and its application. The drawings are intended only to illustrate the invention and they constitute only one of its many possible implementations.

THE INVENTION

Figure 1:
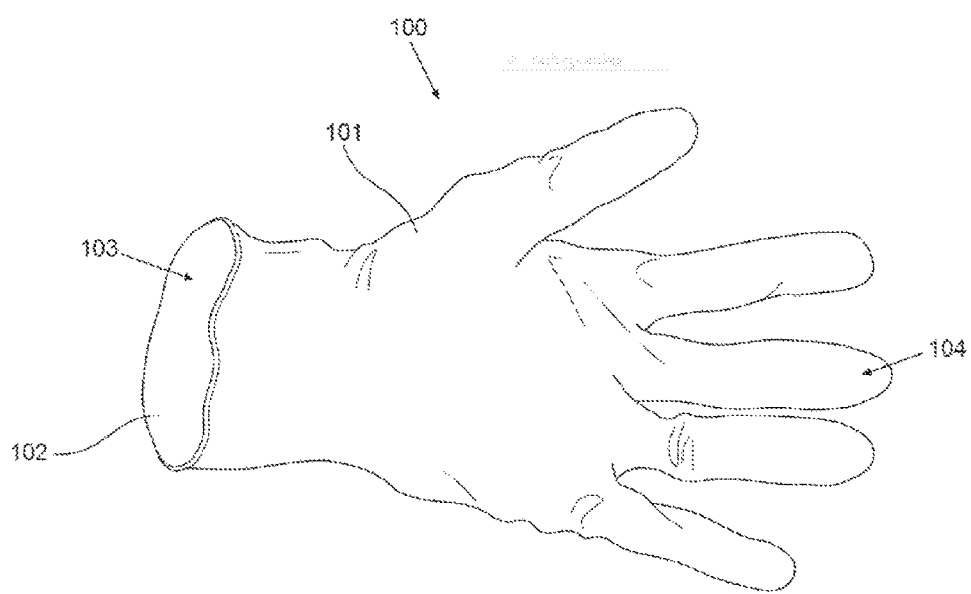
FIG. 1 depicts a standard sterile glove (100) with an upper (finger) part (101), a lower (wrist) part (102), and an opening (103).

The main objective of the present invention is to provide a gloving apparatus (1) that is designed to help users put gloves on their hands. The gloving apparatus (1) comprises the following main parts: a box of gloves (2), a glove-lifting device (3), a glove-opening device (4), and a glove-inflating device.

The glove box (2) is designed to contain gloves, specifically sterile gloves. The gloves are placed in the box, open and flat, one on top of the other. The glove to box may a fixed and permanent part of the gloving apparatus that is refilled whenever the gloves run out, or, alternatively, the entire box may be replaced with a new glove box, thus serving as a kind of disposable glove cartridge. In cases in which the sterility of the gloves must be maintained, the disposable, replaceable glove box setup is more appropriate and recommended.

The glove-lifting device (3) is designed to lift gloves from the glove box (2), one glove at a time, and to position the glove opening (103) over the glove-opening device (4), thus starting the process of putting the glove on the user's hand. The glove-lifting device (3) consists of a vertical rod (31), whose lower end is equipped with a fastening means (32), which can be, for instance, a small suction cup. The glove-lifting device (3) can and should, in fact, be equipped with two fastening means (32).

The vertical rod (31) descends to a position in which the fastening means (32) comes in contact with the upper back part (101) of the topmost glove (100) in the glove box (2), at which point the fastening means (32) pick the glove up. The vertical rod (31) then rises, taking the said glove (100) with it so that the glove opening (103) is opens slightly due to the pull of gravity on the lower back part (102) of the glove opening (103).

The glove-lifting device (3) then retracts in a horizontal motion and inserts the glove opening (103) over the glove-opening device (4). The glove-lifting device (3) is also equipped with a vertical activator (33) that lowers and raises the vertical rod (31) and with a horizontal activator (34) that moves the glove (100) in a horizontal motion, inserting it over the glove-opening device (4). For the sake of clarity, FIG. 1 presents the parts of the glove (100) and their respective numbers.

The glove-opening device (4) comprises four spreading fingers (41) each of which can move both horizontally and vertically, independently from the other three spreading fingers (41). In the starting position, the four spreading fingers (41) are joined together to form a pin-like structure. As mentioned, the glove-lifting device (3) lifts the glove (100) and positioned it so that its opening (103) is inserted over the spreading fingers (41).

The spreading fingers (41) then move away from each other, stretching the opening (103) of the glove (100) open until the resulting square-shaped opening (103) is wide and can accommodate the easy insertion of a person's hand. The two right-hand spreading fingers first move to the right, while the two left-hand spreading fingers move to the left, and at the same time, or immediately following the lateral motion, the two upper spreading fingers move upward, while the two lower spreading fingers move downward, thus stretching the glove opening (103) to the above-mentioned position. The glove-opening device (4) is equipped with activators (42) that are designed to move the spreading fingers (41) up, down, and to the sides. Each spreading finger (41) should be equipped with two activators.

The glove-inflating device (5) comprises a sealing ring (51), an air tubule (52), and an activator (53). The sealing ring (51) moves horizontally between the spreading fingers (41) and is inserted slightly into the opening (103) of the glove (100). The activator (53) of the glove-inflating device (5) leads the sealing ring (51) into the glove opening (103) so that the interior of the glove closes over the sealing ring (51). Air flows through the air tubule (52) into the interior of the glove (100) and inflates it.

The air tubule (52) may be a thin air duct that is built into the sealing ring (51) and through which air flows into the glove through one or more apertures (54). Air can be pumped into the glove using a bellows or blower or any other appropriate mechanism. After the glove (100) is inflated, the user may insert his or her hand through the sealing ring (51) until the hand is fully inserted into the glove (100).

In order to facilitate the inflation of the glove (100) and to prevent air from escaping out of the inflated glove, the middle part of the sealing ring (51) may be closed with a flexible membrane (55) with a central hole (56) through which the user inserts his or her hand into the inflated glove (100). In this way, the air flow inflates the glove and when the user inserts his or her hand through the central hole (56), the seal is strengthened, causing the glove (100) to inflate to a size that exceeds that of a standard hand, enabling the user to insert his or her fingers into the glove fingers in a fast, effective, easy and complete manner.

After the user's hand is inserted into the glove (100) as described above, the spreading fingers (41) move up and down, and the sealing ring (51) retracts and is released from the glove, which now moves forward and is released from the hold of the spreading fingers (41). The glove (100) is now completely applied over the user's hand, and the user can pull his or her gloved hand out of the apparatus.

In order to release the edge of the glove's opening (103) from the sealing ring (51), the sealing ring may retract until the edge of the opening (103) is released from the sealing ring (51).

The gloving apparatus (1) may be equipped with two glove boxes (2): one that contains right-hand gloves and another that contains left-hand gloves. The apparatus (1) can also be equipped with a mechanism that positions the appropriate box according to need. In other words, when the user wishes to apply a glove to his or her right hand, or left hand, the user presses a button that positions the correct glove box in the correct location for the glove-lifting device.

The gloving apparatus (1) may also be equipped with controllers and sensors that enable it to operate rapidly and in the correct order, according to the required action. Thus, for instance, the apparatus might have an activation sensor (61) that identifies the hand when it approaches or is inserted into the sealing ring (51) and activates the glove-lifting device (3), which lifts a glove and places it on the spreading fingers (41), which in turn move sideways and up and down, after which the sealing ring (51) moves forwards and the glove opening (103) is inserted over the sealing ring (51), as described above.

The gloving apparatus (1) may also be equipped with a mechanical or electric button that activates the system without the need for an activation sensor (61). The gloving apparatus (1) may also be equipped with a gloving completion sensor (62), which identifies the moment the hand is fully inserted into the glove (100) and releases the glove from the sealing ring (51) in a way that enables the user to pull his or her gloved hand out of the apparatus. The gloving completion sensor (62) may be an optic sensor that identifies the forward motion of the glove fingers, which may indicate that the hand is fully within the glove. Specifically, when the glove is inflated, the ends of the inflated glove fingers extend out to a certain point. When the user inserts his or her hand into the fingers of the glove, he or she slightly pushes the ends of the glove's fingers forward, and so the gloving completion sensor (62) may be based on an optic beam that identifies this motion and activates the above-mentioned end stages. Alternatively, the release action might be based on a timer that indicates the execution of the end stages, within a time frame of several seconds from the beginning of the operation of the apparatus (1), assuming that the gloving action is completed within this time period. The gloving apparatus (1) may also be equipped with indication lamps; for instance, a green light might indicate to the user that he or she may insert their hand through the sealing ring and a red light might indicate it is time the user pulls his or her gloved hand out of the apparatus.

Figure 2:
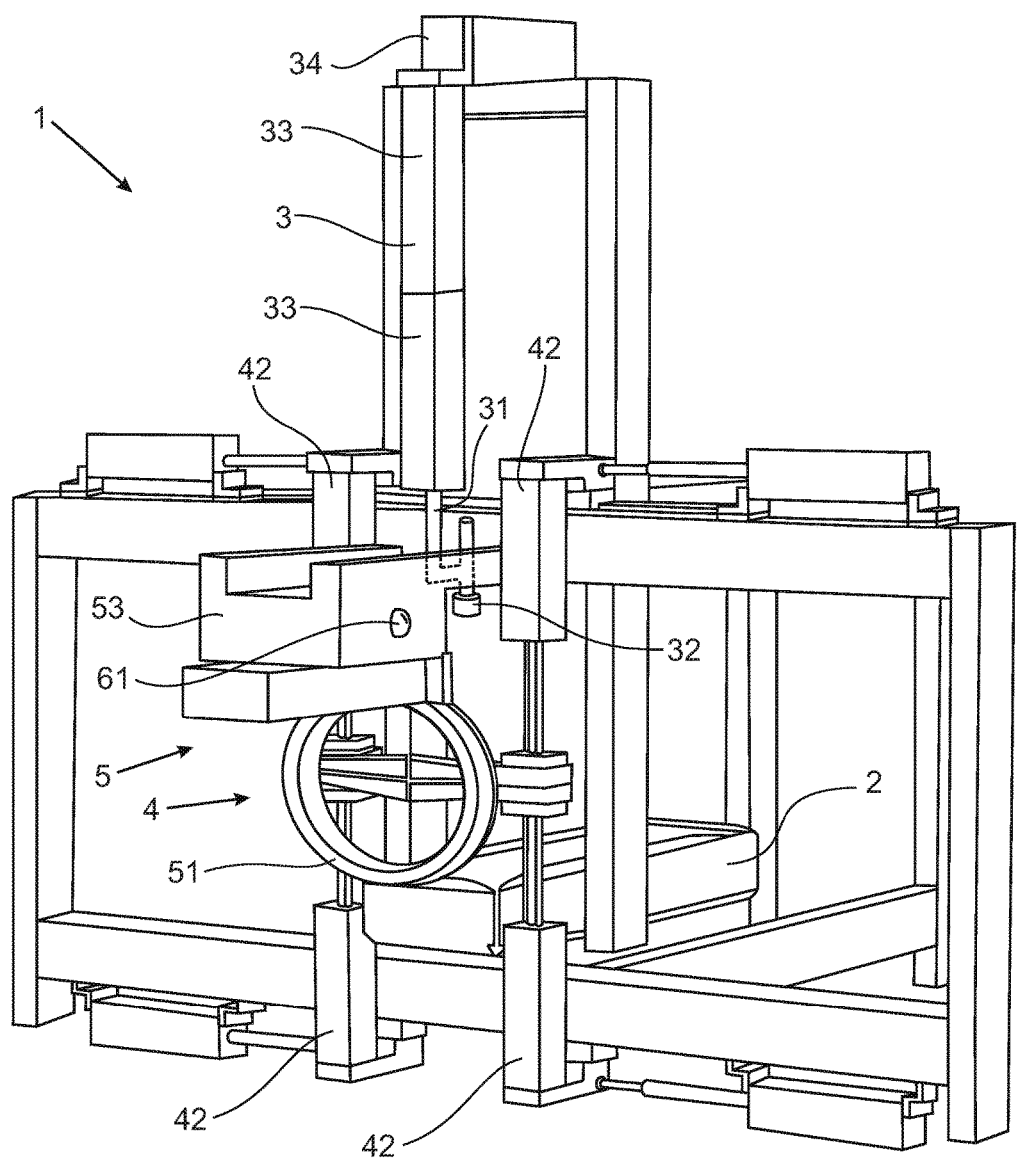
FIG. 2 depicts the gloving apparatus (1), which comprises a glove box (2), a glove-lifting device (3), a glove-opening device (4), and a glove-inflating device glove (5).

FIG. 2 depicts the gloving apparatus (1) devoid of any casing or shell so as to reveals its inner parts. FIG. 2 depicts the main parts of the gloving apparatus (1), which include a glove box (2), a glove-lifting device (3), a glove-opening device (4), and a glove-inflating device (5).

The gloving apparatus depicted in FIG. 2 is depicted in starting position, before going into action and gloving the user's hand.

Figure 3:
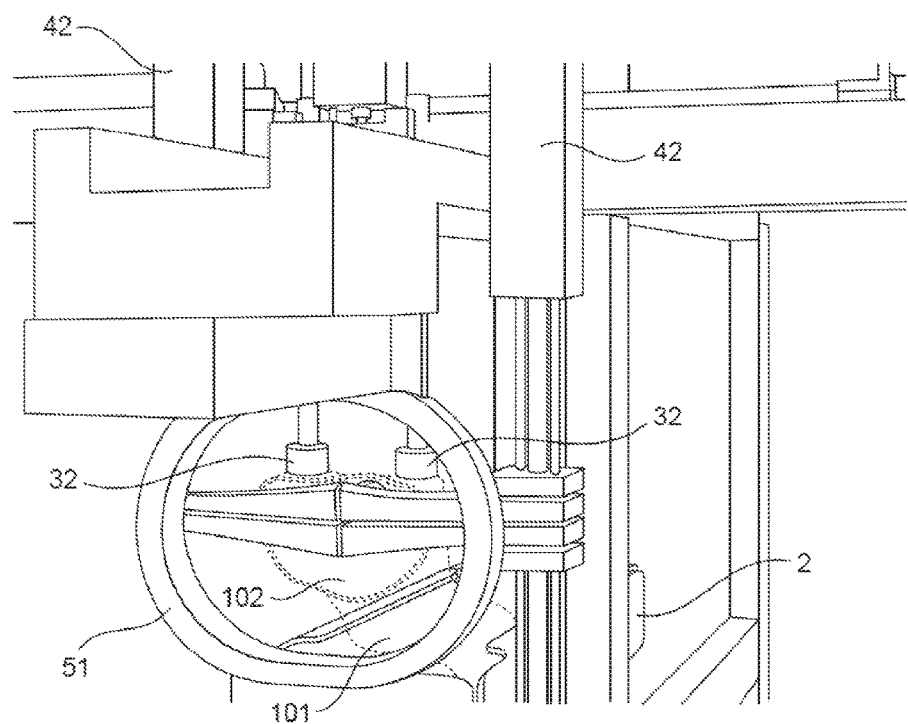
FIG. 3 depicts the gloving apparatus (1) wherein the glove-lifting device (3) is holding a glove (100), and the glove opening (103) is opened.
Figure 4:
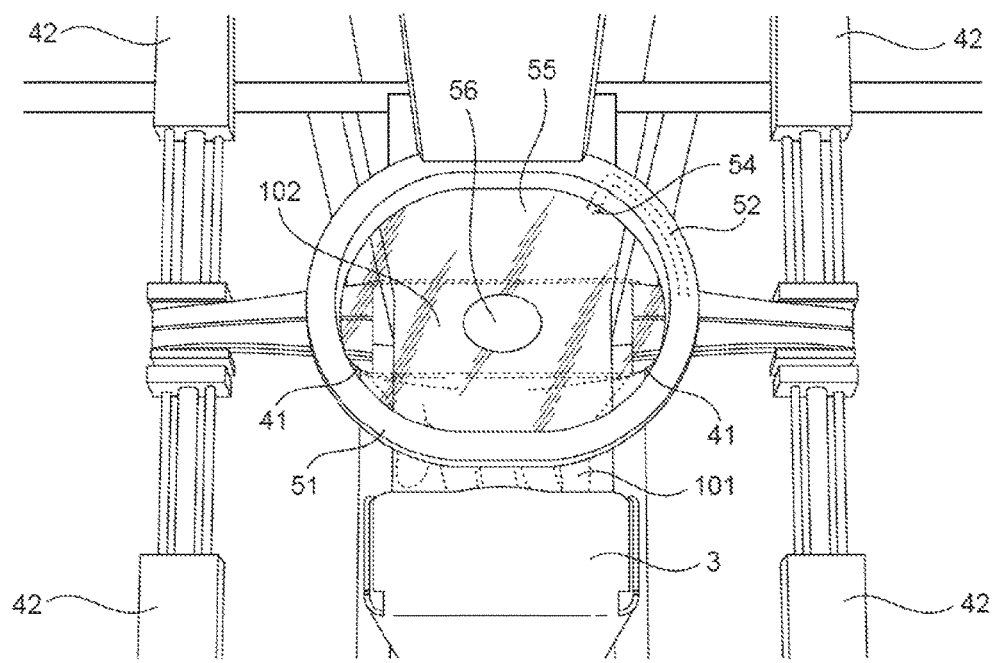
FIG. 4 depicts the gloving apparatus (1) wherein the opening (103) of the glove (100) is inserted over the spreaders (41), which are still closed position.
Figure 5:
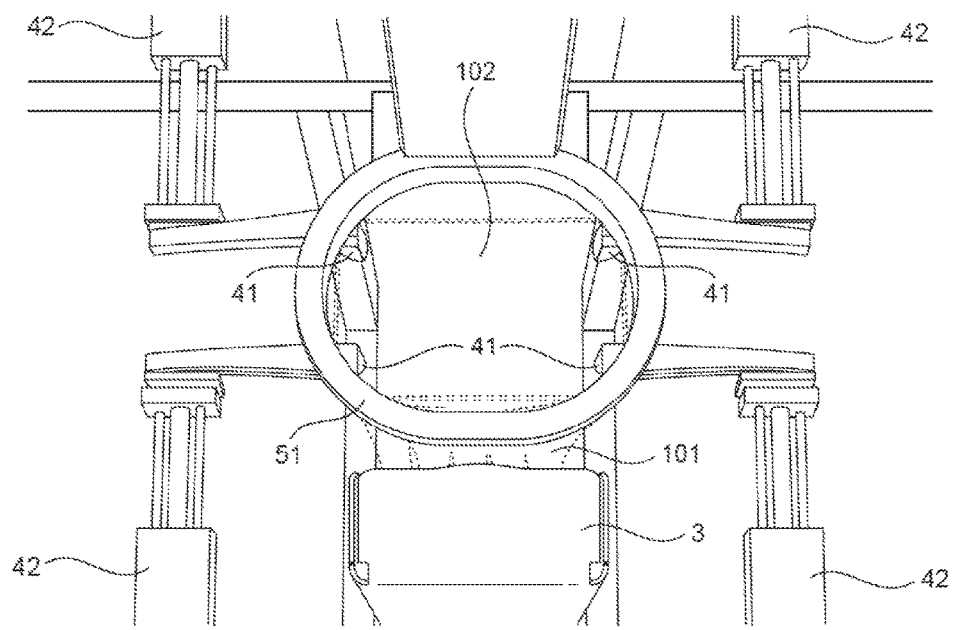
FIG. 5 depicts the gloving apparatus (1) wherein the spreading fingers (41) have stretched open the glove opening (103).
Figure 6:
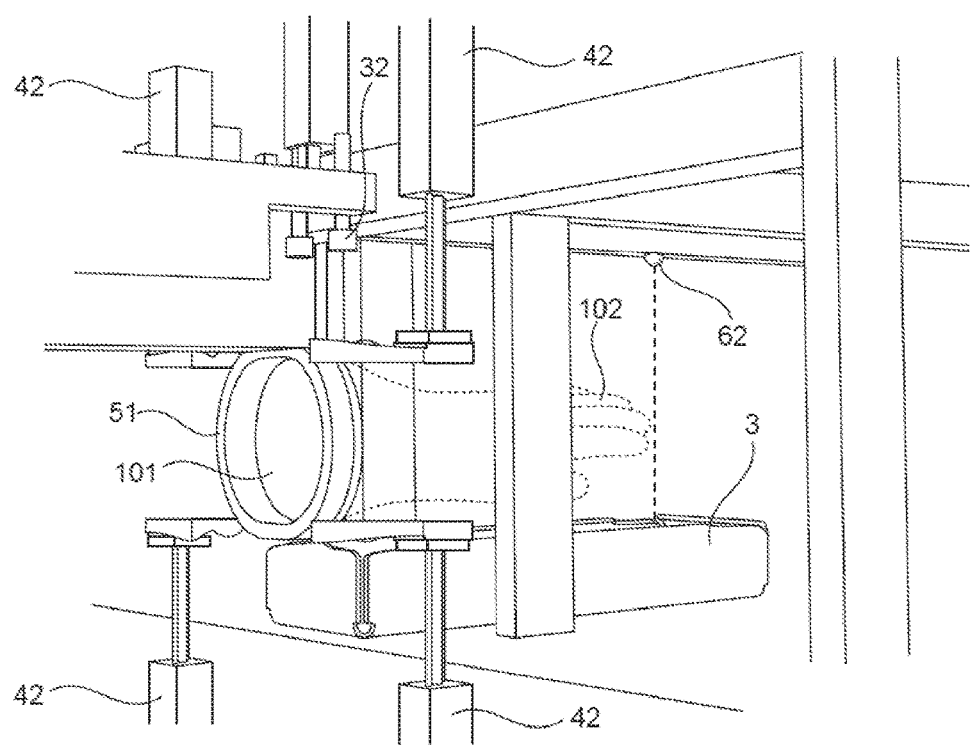
FIG. 6 depicts the gloving apparatus (1) wherein the edge of the glove's opening (103) is inserted over the sealing ring (51) and the glove is inflated into a hand-shape "balloon".
Figure 7:
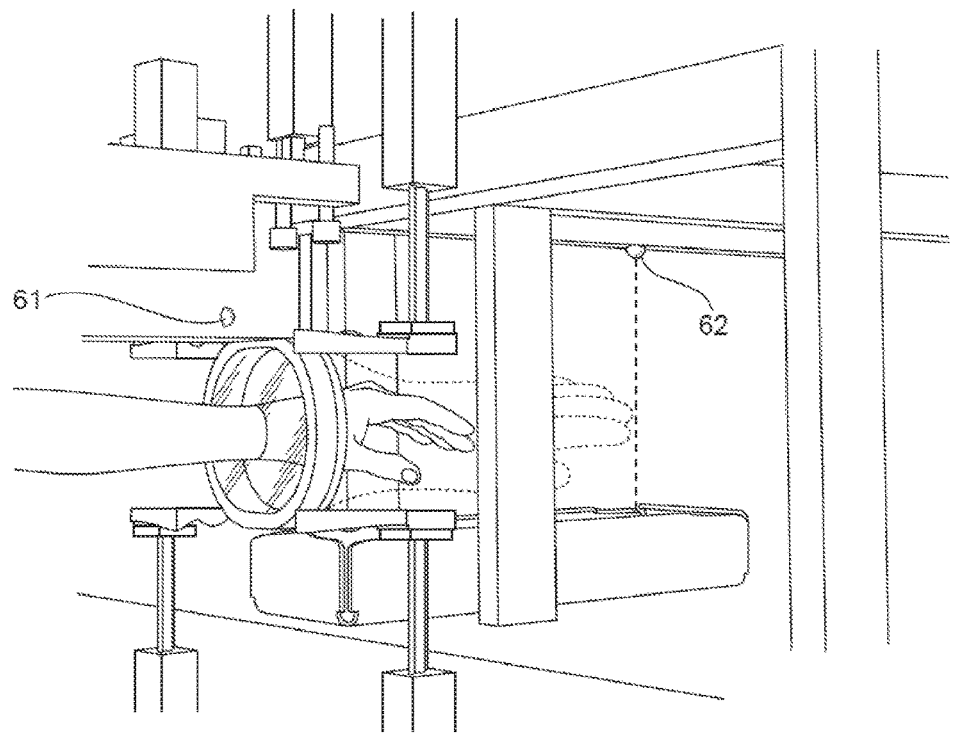
FIG. 7 depicts the gloving apparatus (1) wherein the glove (100) is inflated and the user is inserting his or her hand into the inflated glove, which is still being held by the gloving apparatus (1).
Figure 8:
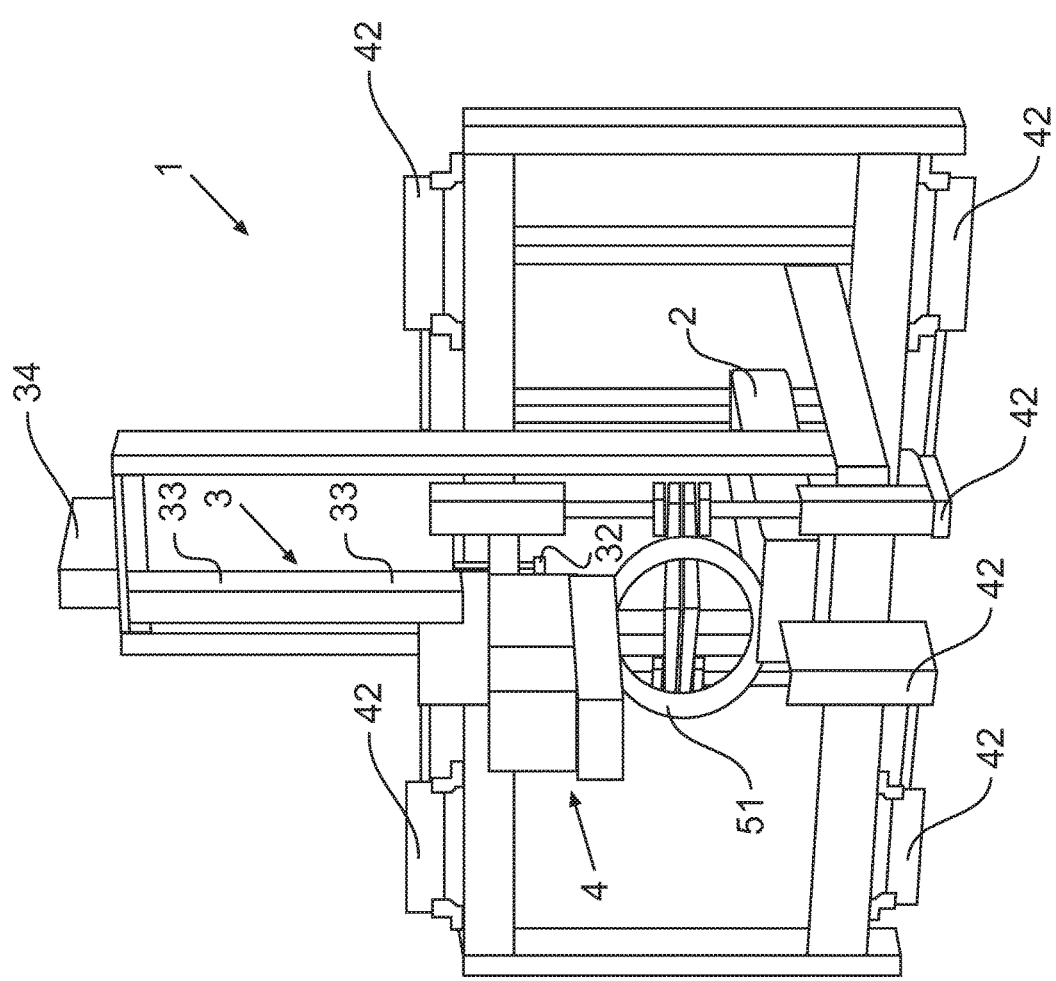
FIGS. 8-11 depict the gloving apparatus (1) and its parts from several viewpoints.
Figure 9:
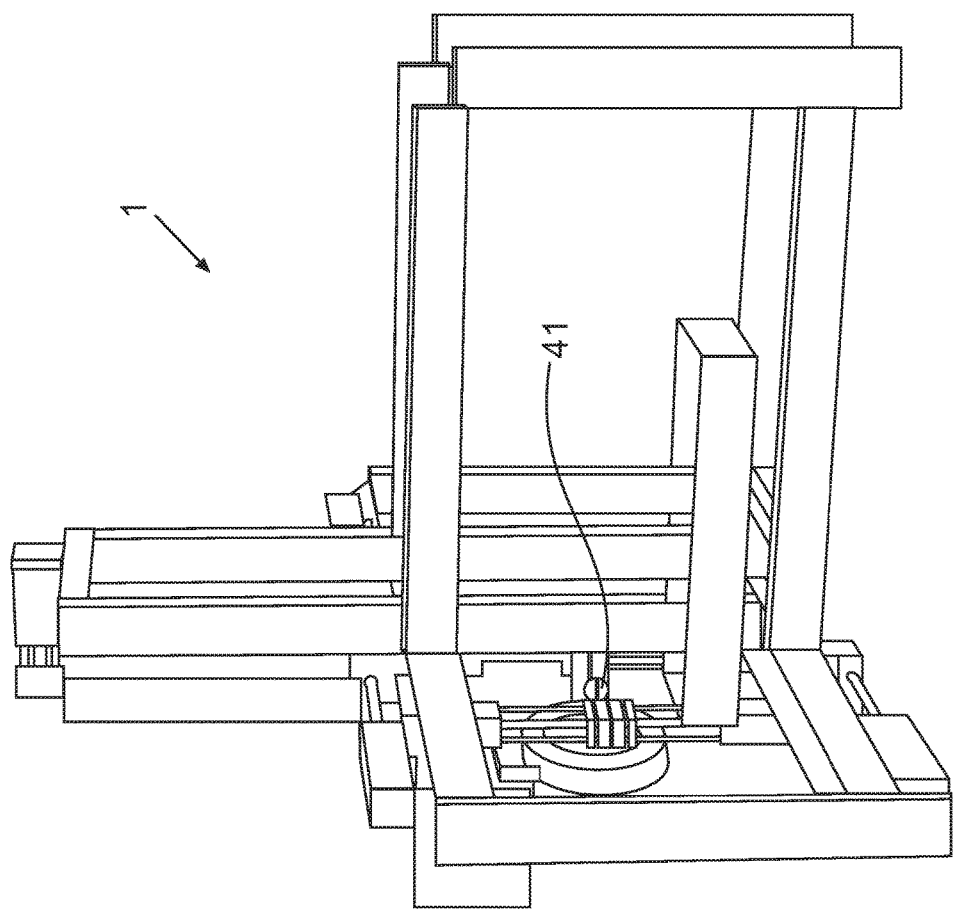
Figure 10:
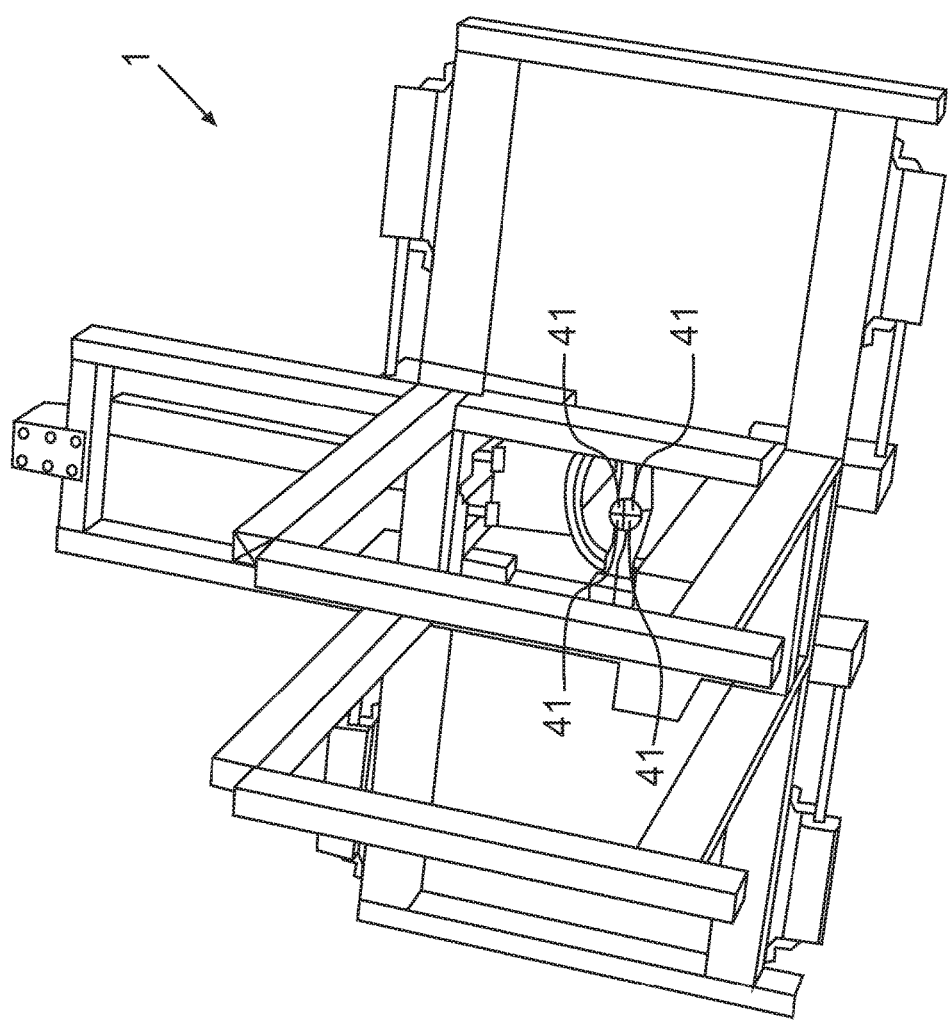
Figure 11:
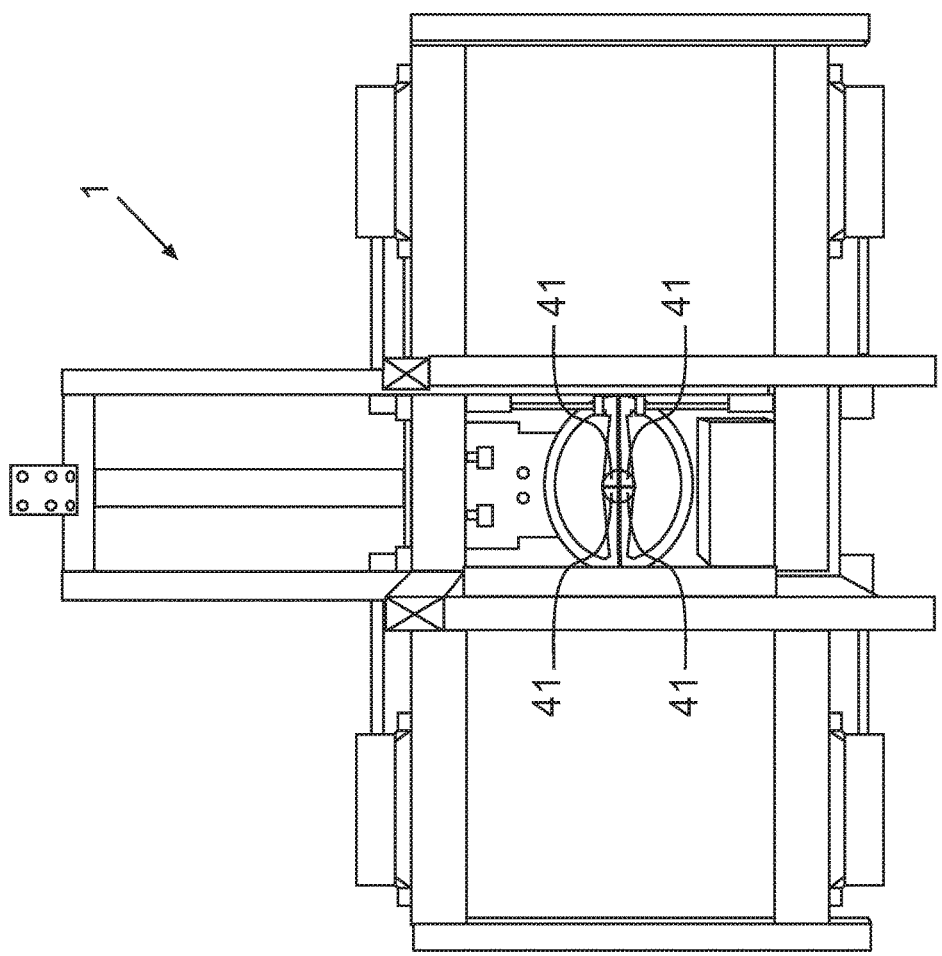

FIG. 3 depicts the gloving apparatus (1) wherein the glove-lifting device (3) is holding a glove (100), and the glove opening (103) is opened. FIG. 4 depicts the gloving apparatus (1) wherein the opening (103) of the glove (100) is inserted over the spreading fingers (41), which are still in closed position. FIG. 5 depicts the gloving apparatus (1) wherein the spreading fingers (41) have stretched the opening (103) open. FIG. 6 depicts the gloving apparatus (1) wherein the edge of the glove's opening (103) is inserted over the sealing ring (51) and the glove is inflated into a hand-shape "balloon". FIG. 7 depicts the gloving apparatus (1) wherein the glove (100) is inflated and the user's hand is inserted into it, before the glove is released onto the user's hand. FIGS. 8-11 depict the gloving apparatus (1) and its parts from several viewpoints.

Figure 12:
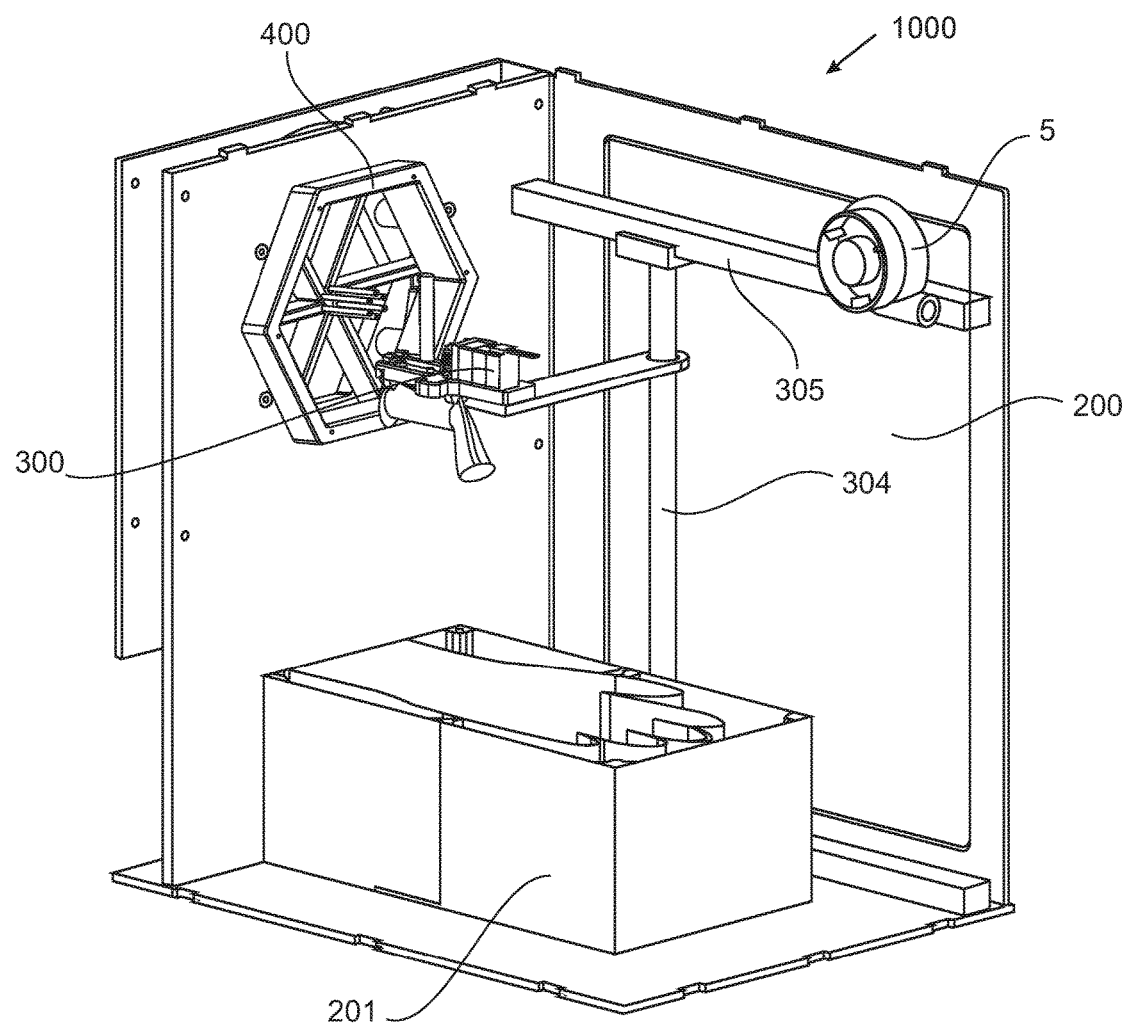
FIGS. 12-27 depict the gloving apparatus (1000) and its parts from several viewpoints.
Figure 13:
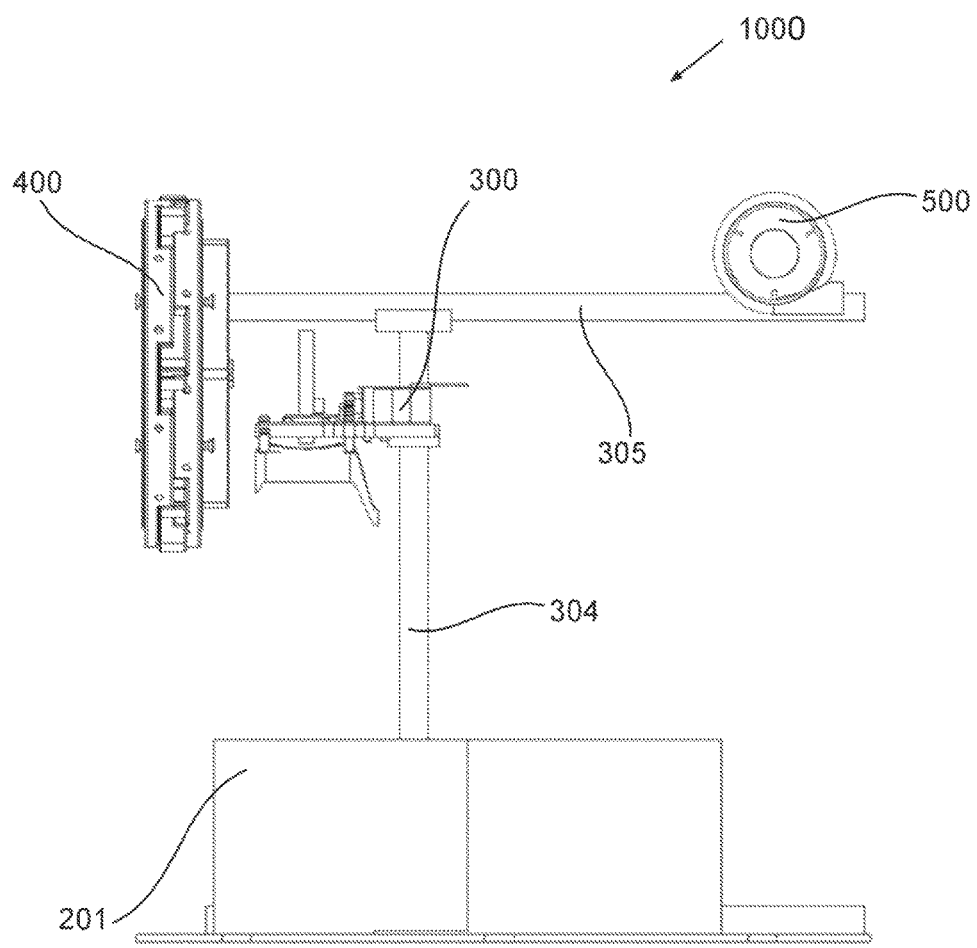
Figure 14:
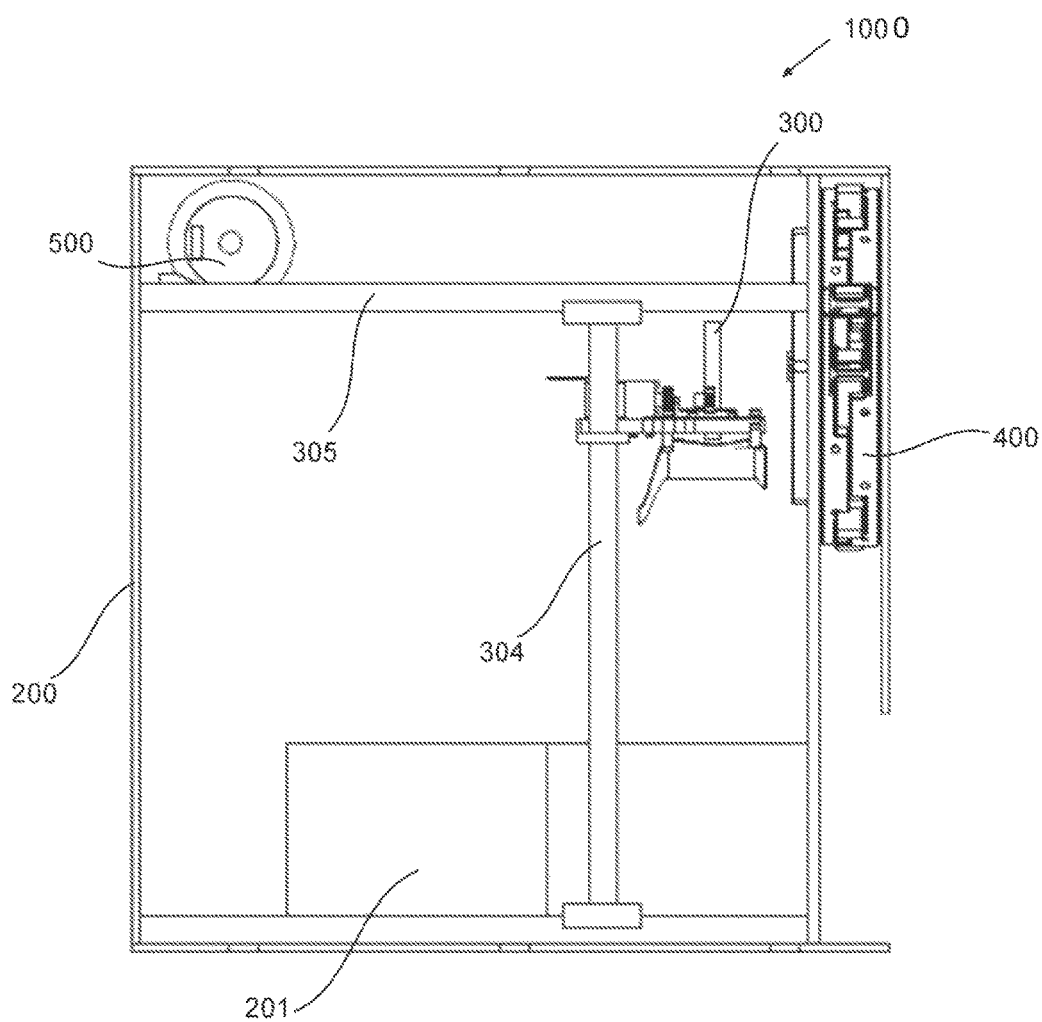

The second version of the invention refers to a gloving apparatus (1000) as depicted in FIGS. 12 to 27. The gloving apparatus (1000) includes a casing (200), a glove-lifting-and-positioning device (300), a glove-opening device (400), and a glove-inflating device (500). The casing (200) is partially depicted in FIG. 12, and it contains the above-mentioned parts of the gloving apparatus (1000). The casing (200) may also contain a glove box (201).

The glove-lifting-and-positioning device (300) is depicted in FIGS. 15 to 21, and comprises an activator (301), graspers (302), a vacuum tube (303), a vertical guide (304), and a horizontal guide (305). The activators enable the glove-lifting-and-positioning device (300) to move up and down on the vertical guide (304) as well as back and forth on the horizontal guide (305).

When the glove-lifting-and-positioning device (300) descends and reaches the glove box (201), and the bottom, open end of the vacuum tube (303) touches the glove (100), preferable in the wrist area, the glove (100) is "picked up" by the vacuum tube. This happens thanks to the vacuum in the vacuum tube, which is produced by an internal pump or any other appropriate means, and which produces a sucking action. The glove-lifting-and-positioning device (300) then rises several millimeters so that the vacuum tube (303) holds the glove at the wrist area.

At this stage the glove is hanging in the air and is slightly open due to the pull of gravity on the upper (finger) part of the glove while the bottom (wrist) part of the glove is held by the vacuum tube. In this position, the activator (301) closes the graspers (302), which then grasp the wrist part of the glove. It is noted that the vacuum tube cannot lift the glove more than several millimeters due to the weight of the glove, hence the need for graspers that can grasp and securely lift the glove to the required height. The glove-lifting-and-positioning device (300), whose graspers (302)

are grasping the wrist part of the glove (100), now lifts the glove upward and slightly forwards, presenting the glove to the glove-opening device (400).

Figure 15:
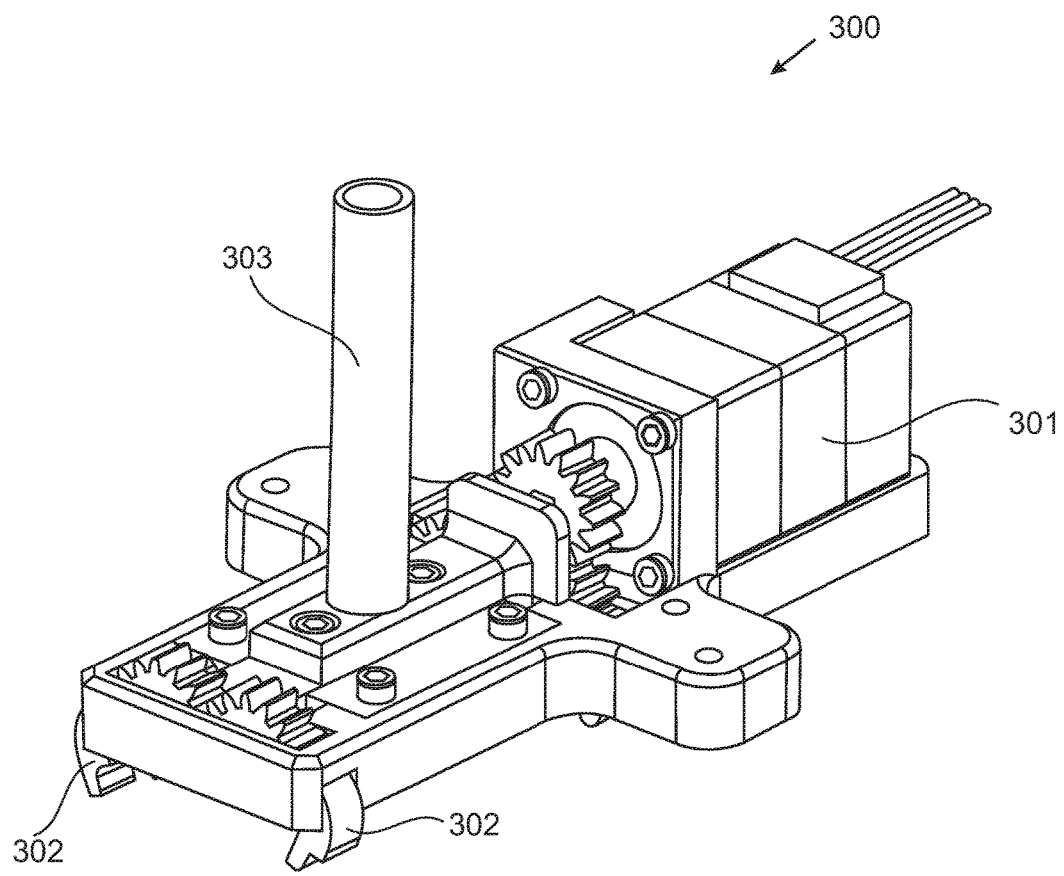
Figure 16:
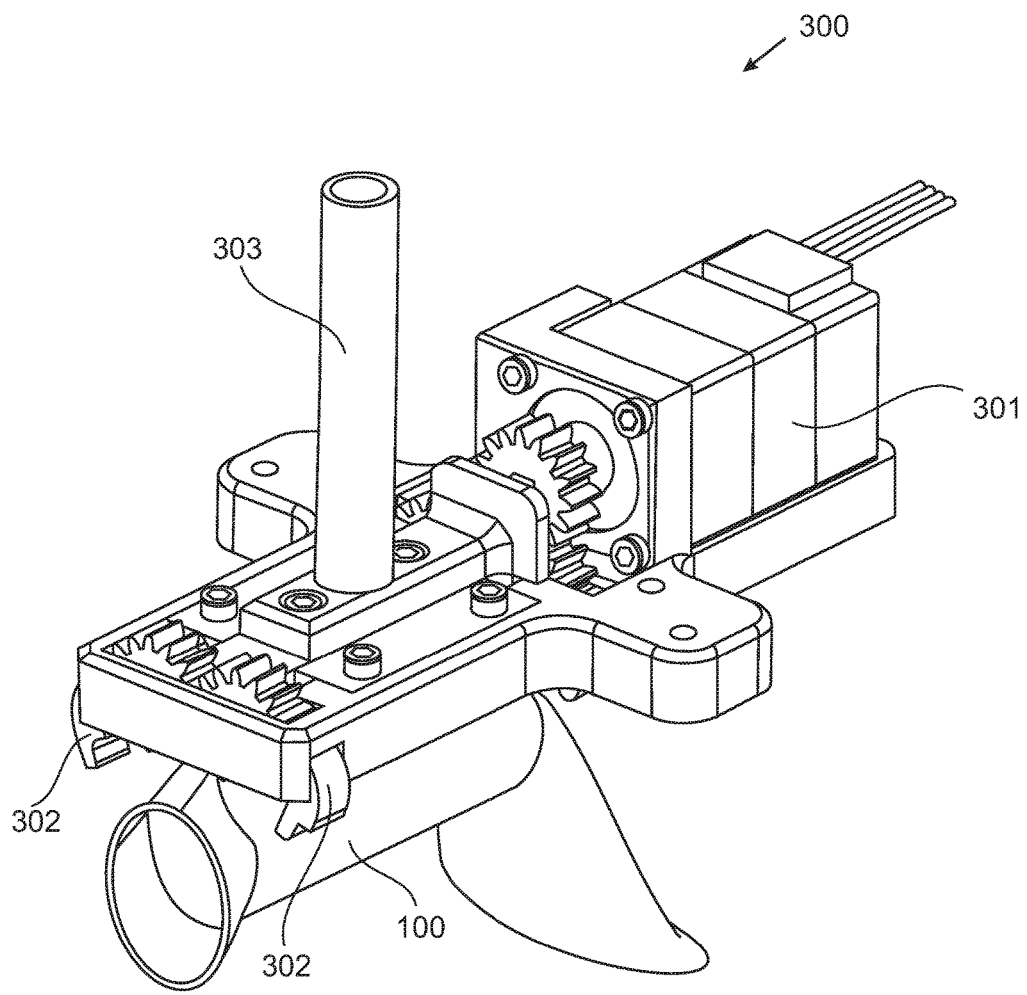
Figure 17:
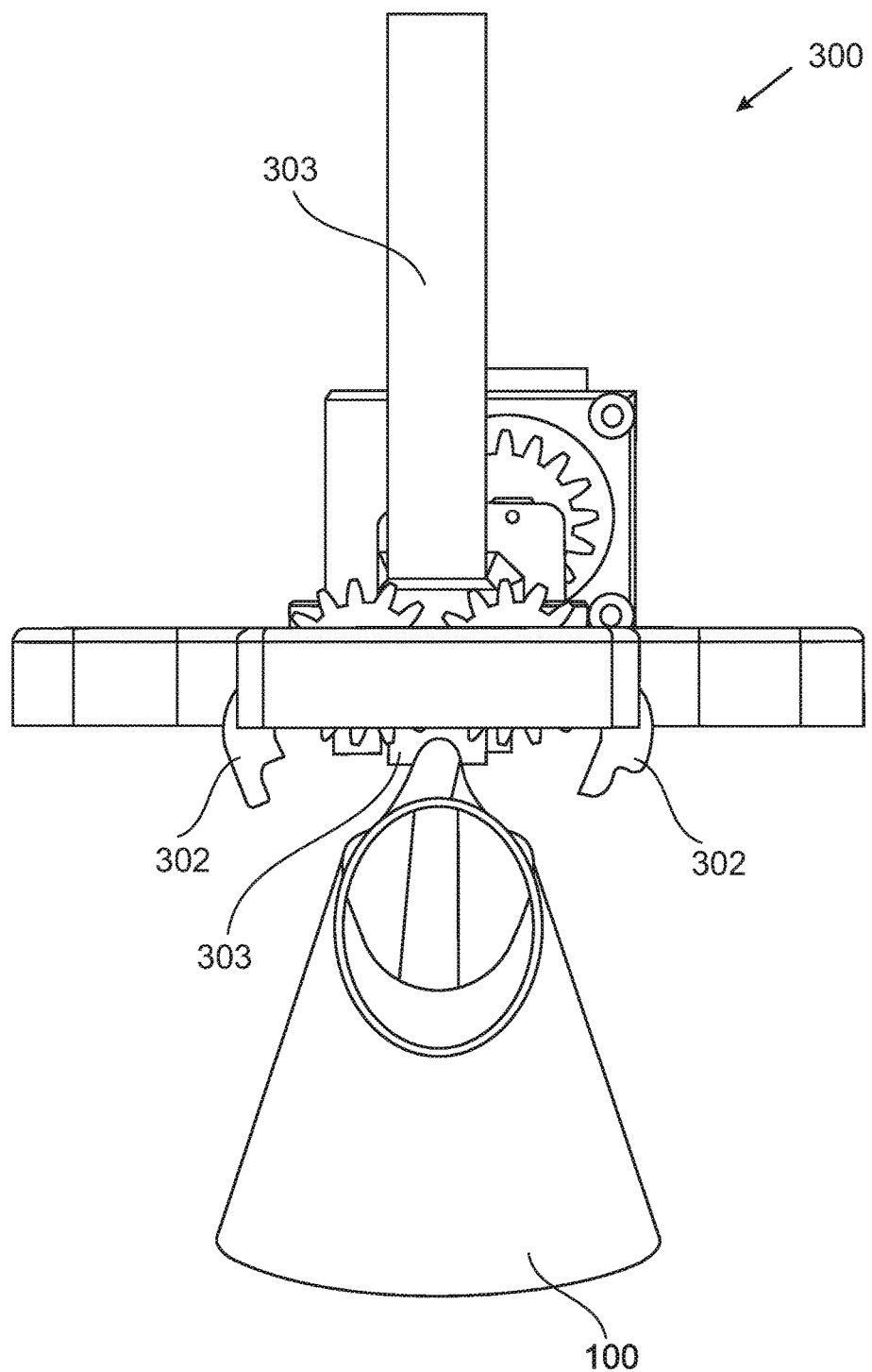
Figure 18:
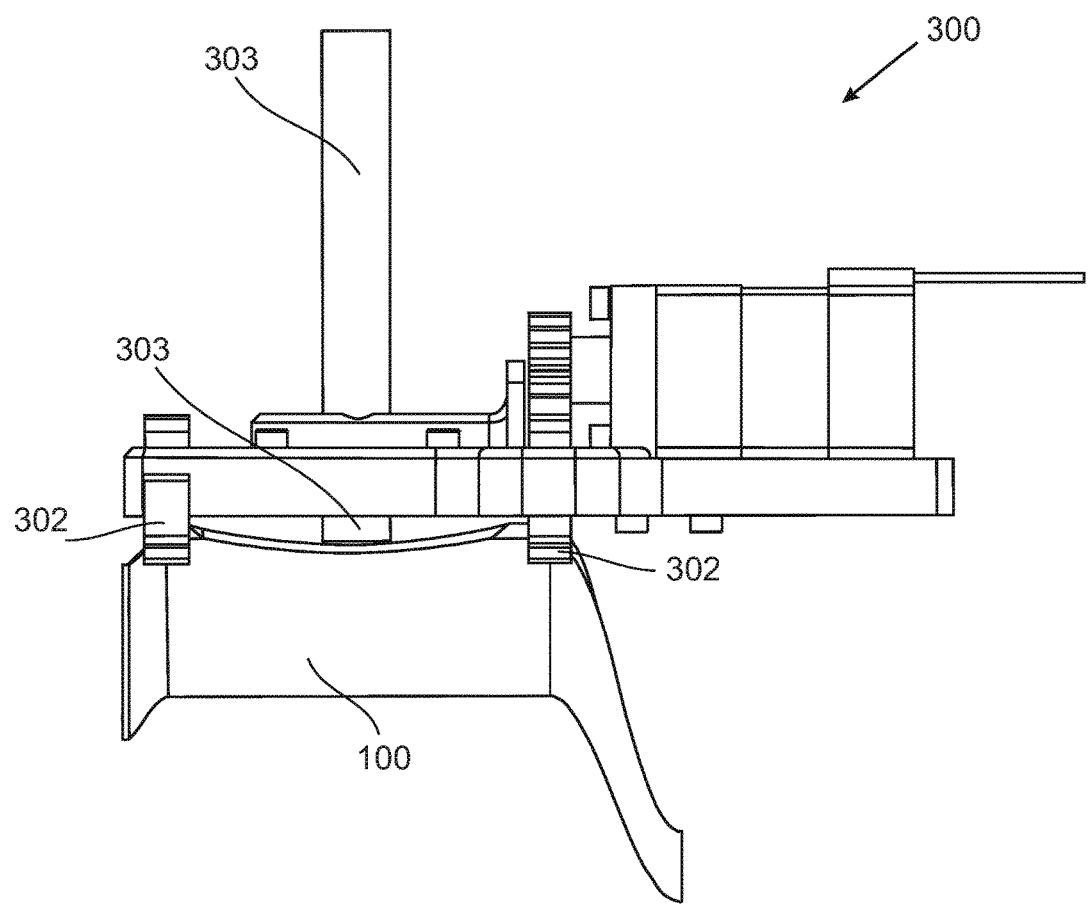
Figure 19:
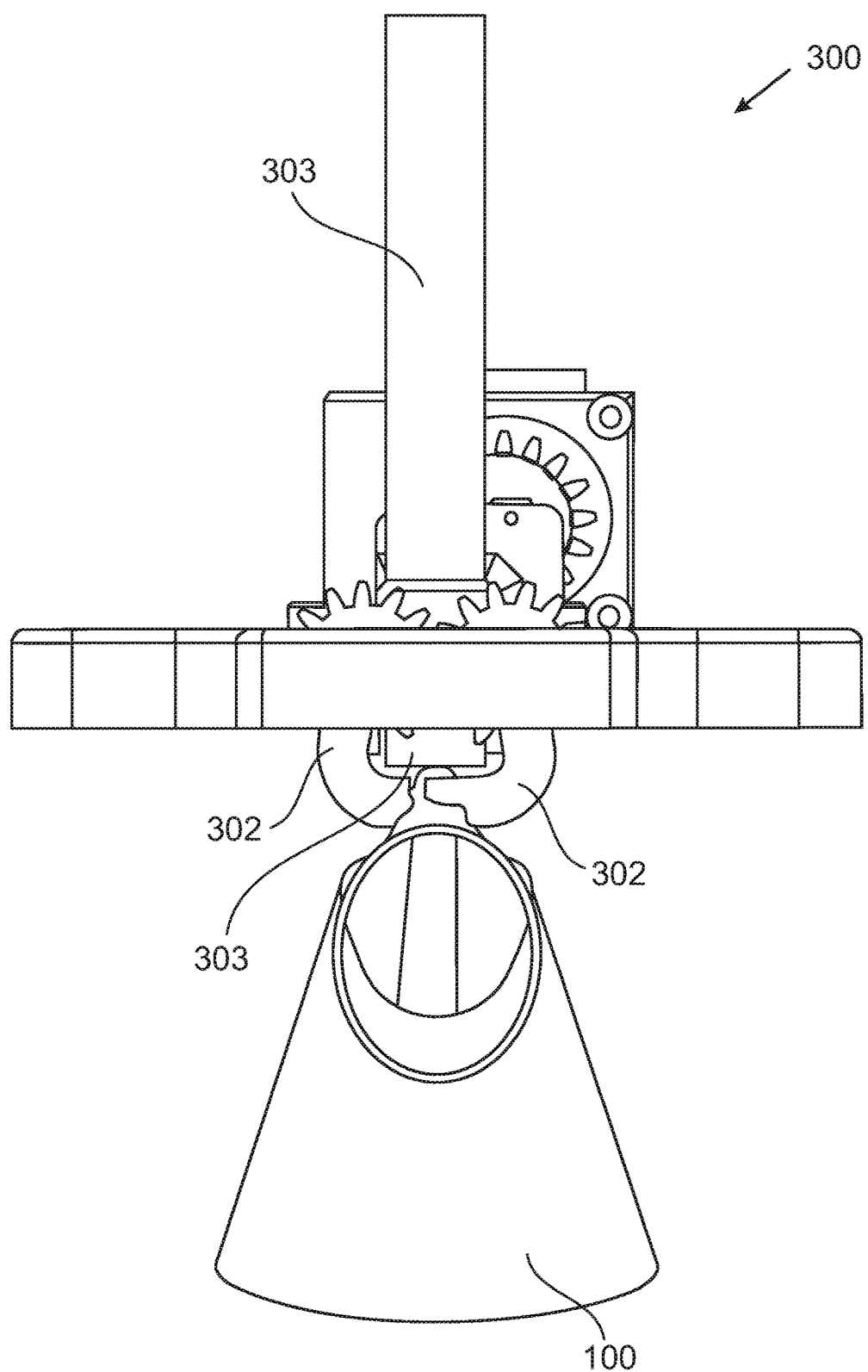
Figure 20:
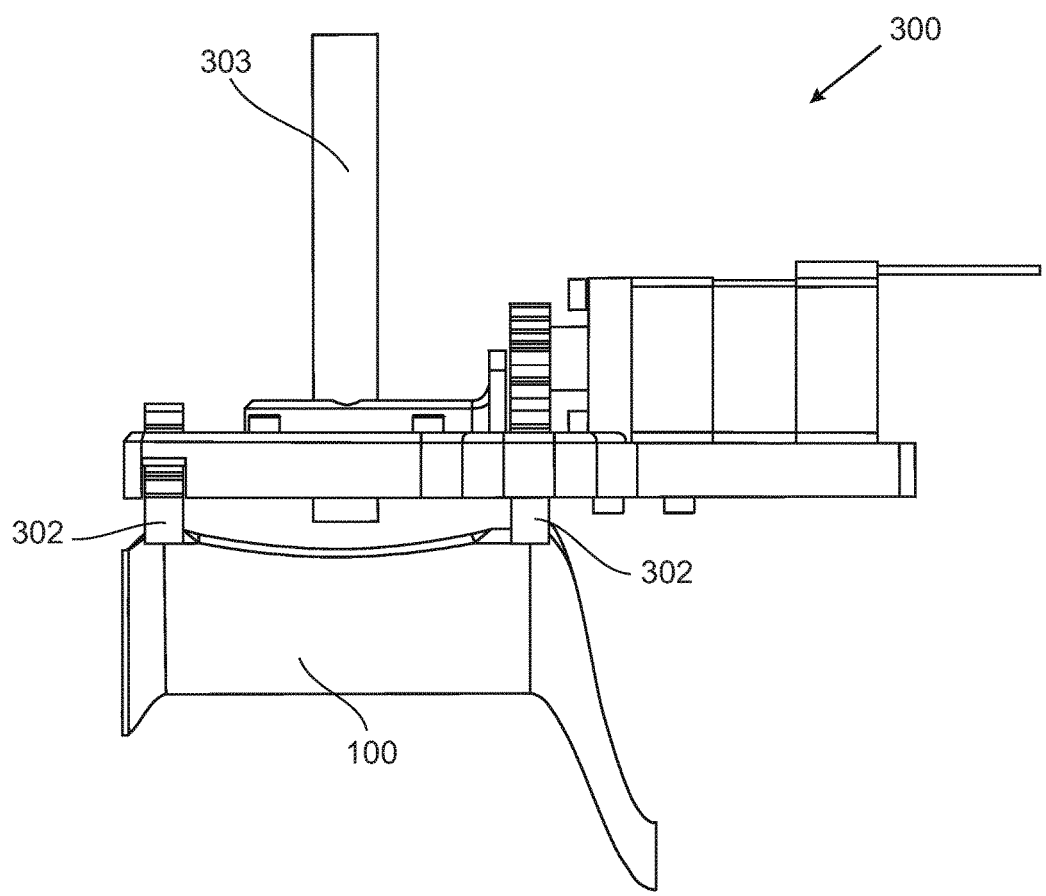
Figure 21:
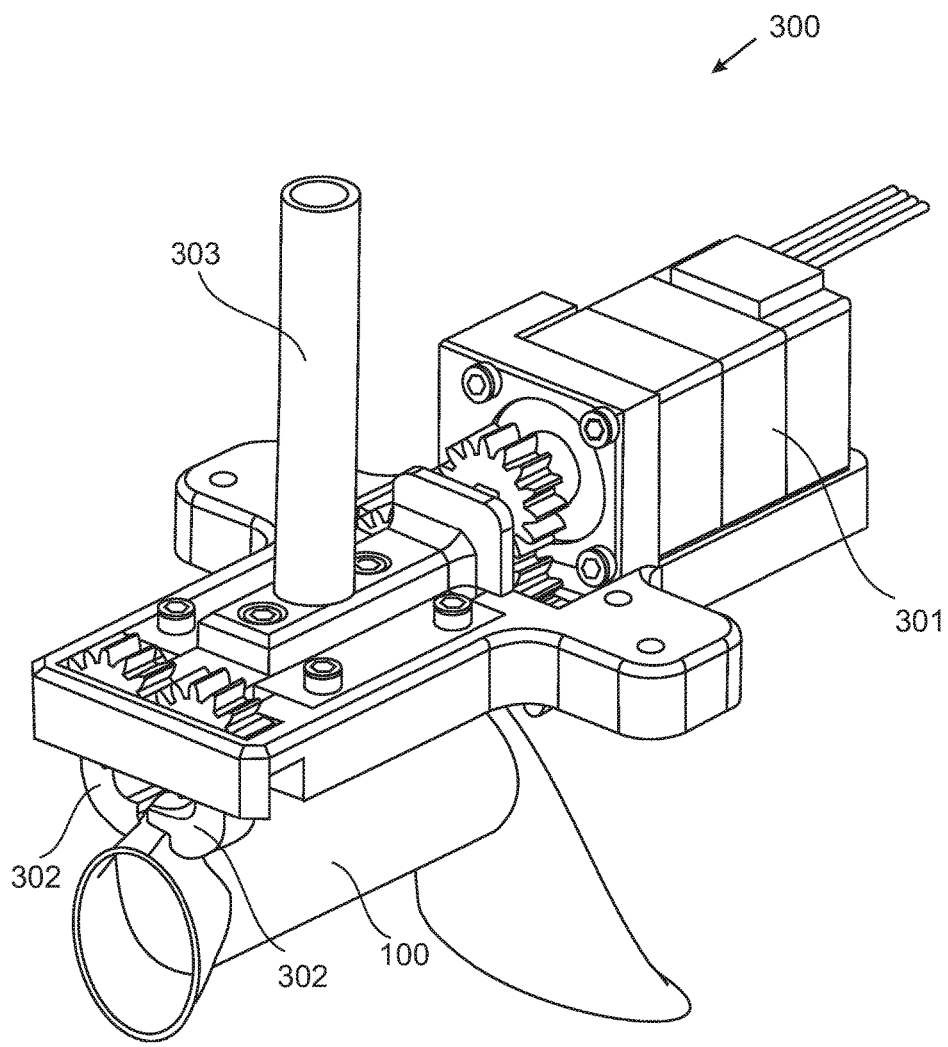

FIG. 15 depicts the glove-lifting-and-positioning device (300), which comprises an activator (301), a vacuum tube (303), and graspers (302) in open position. FIGS. 16 and 17 depict the glove-lifting-and-positioning device (300) with a glove (100) attached to it by means of the vacuum tube (303). FIGS. 18 to 21 depict the glove-lifting-and-positioning device (300) wherein the graspers (302) are holding on to the wrist part of the glove (100).

FIGS. 22 to 27 depict the glove-opening device (400), which includes a polygonal circumferential frame (401) and several spreading rods (402). The number of spreading rods (402) should correspond to the number of sides of the polygonal circumferential frame (401).

The illustrations that accompany this application show a six-sided frame, although the invention may be implemented with a frame with more or less sides. The outer end (403) of each spreading rod (402) is attached to the polygonal circumferential frame (401) via an axial joint.

Figure 22:
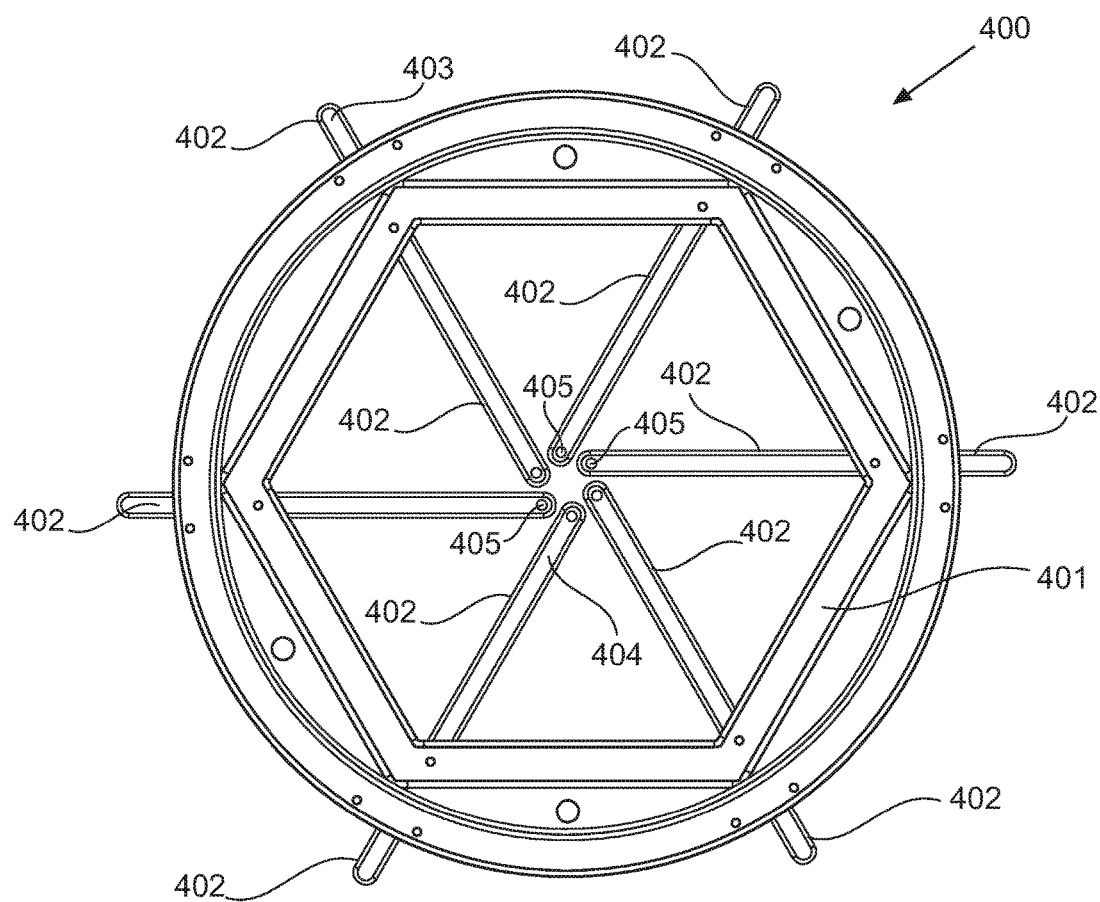
Figure 23:
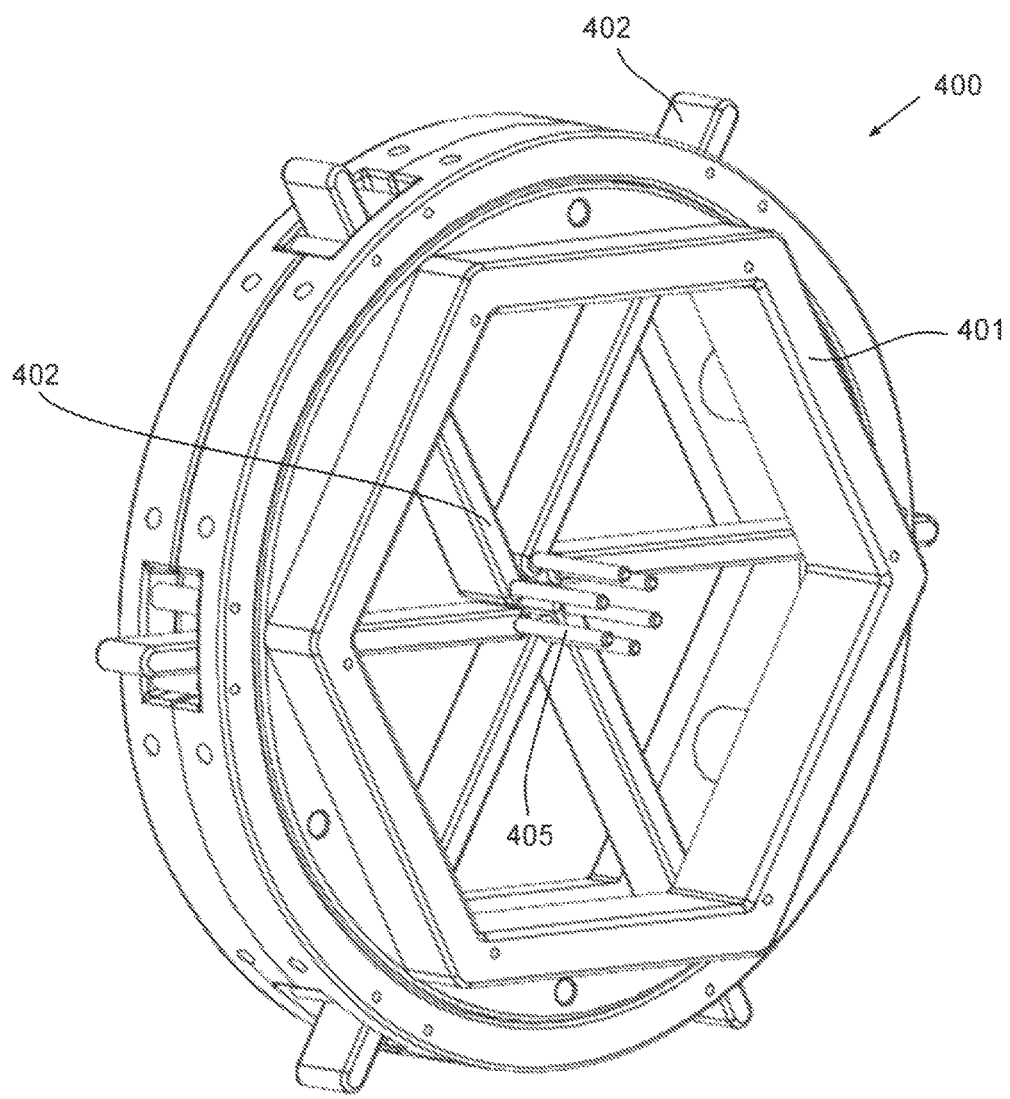
Figure 24:
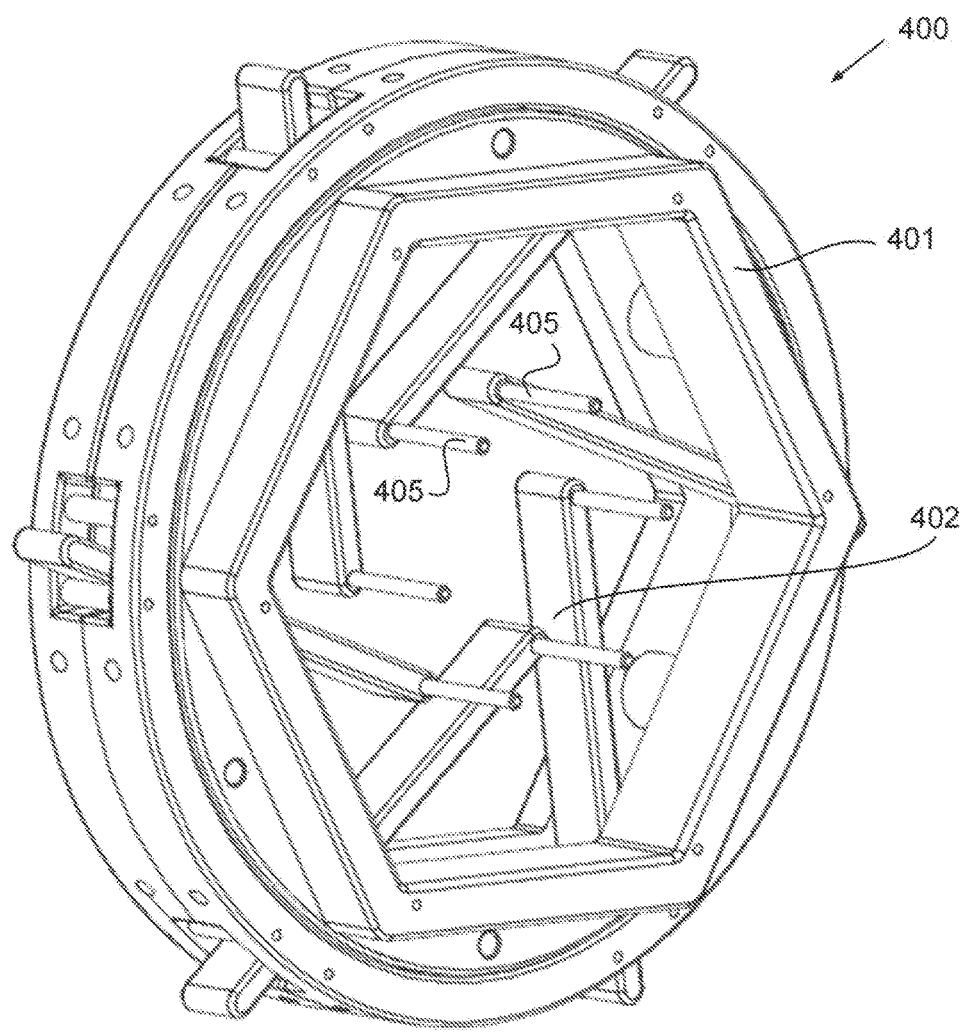
Figure 25:
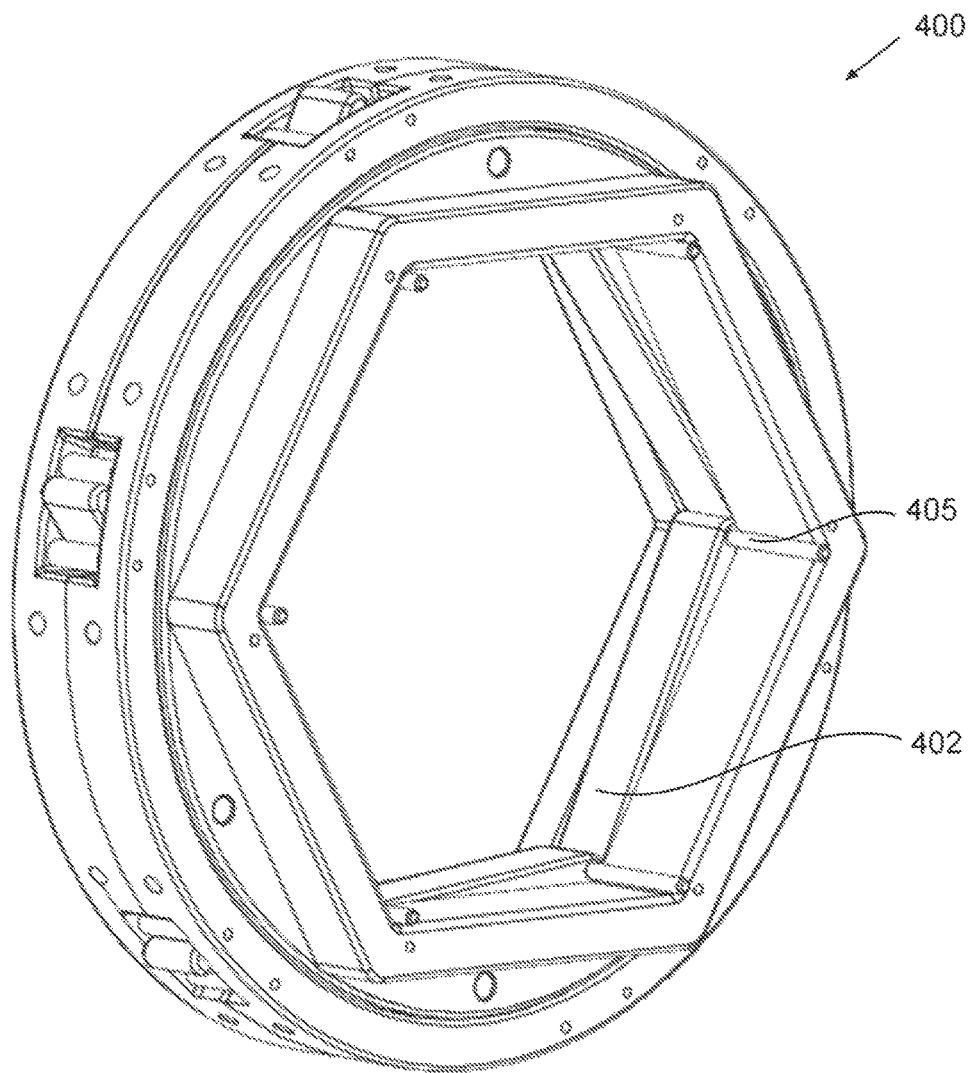
Figure 26:
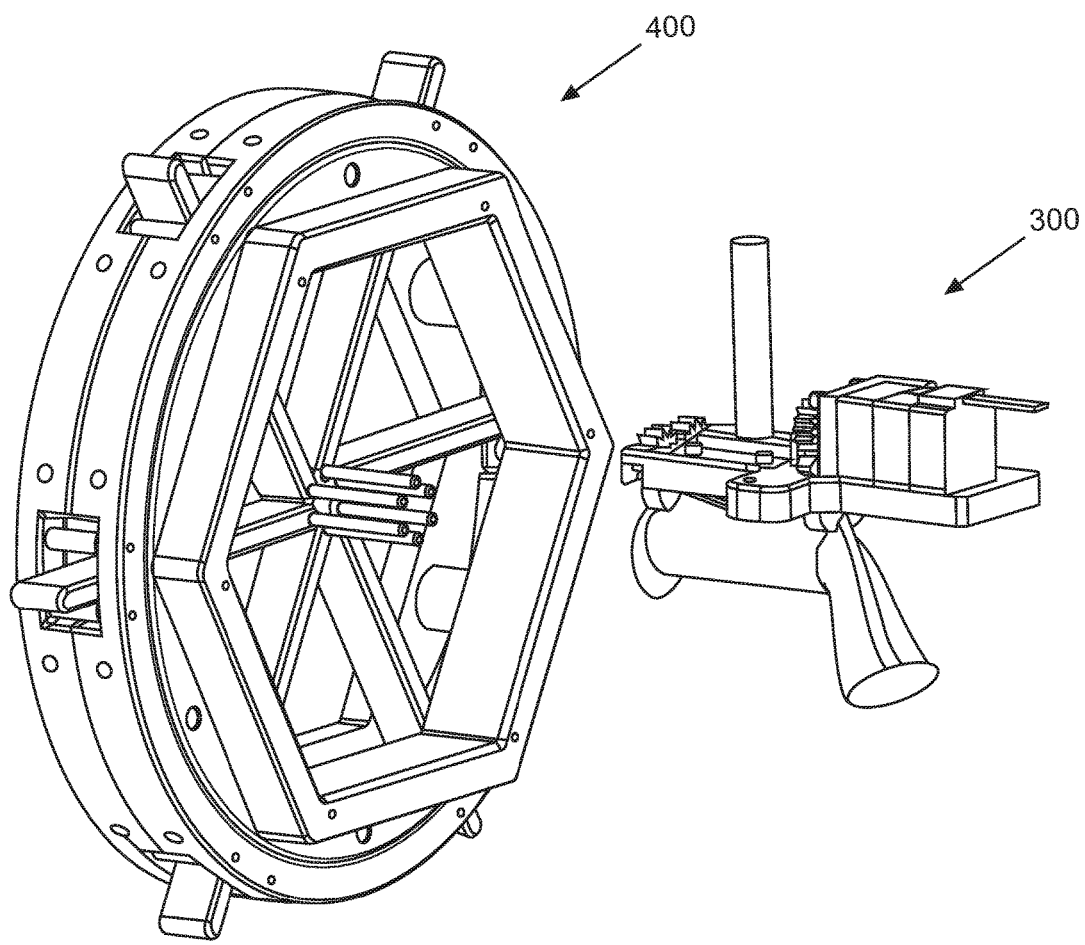
Figure 27:
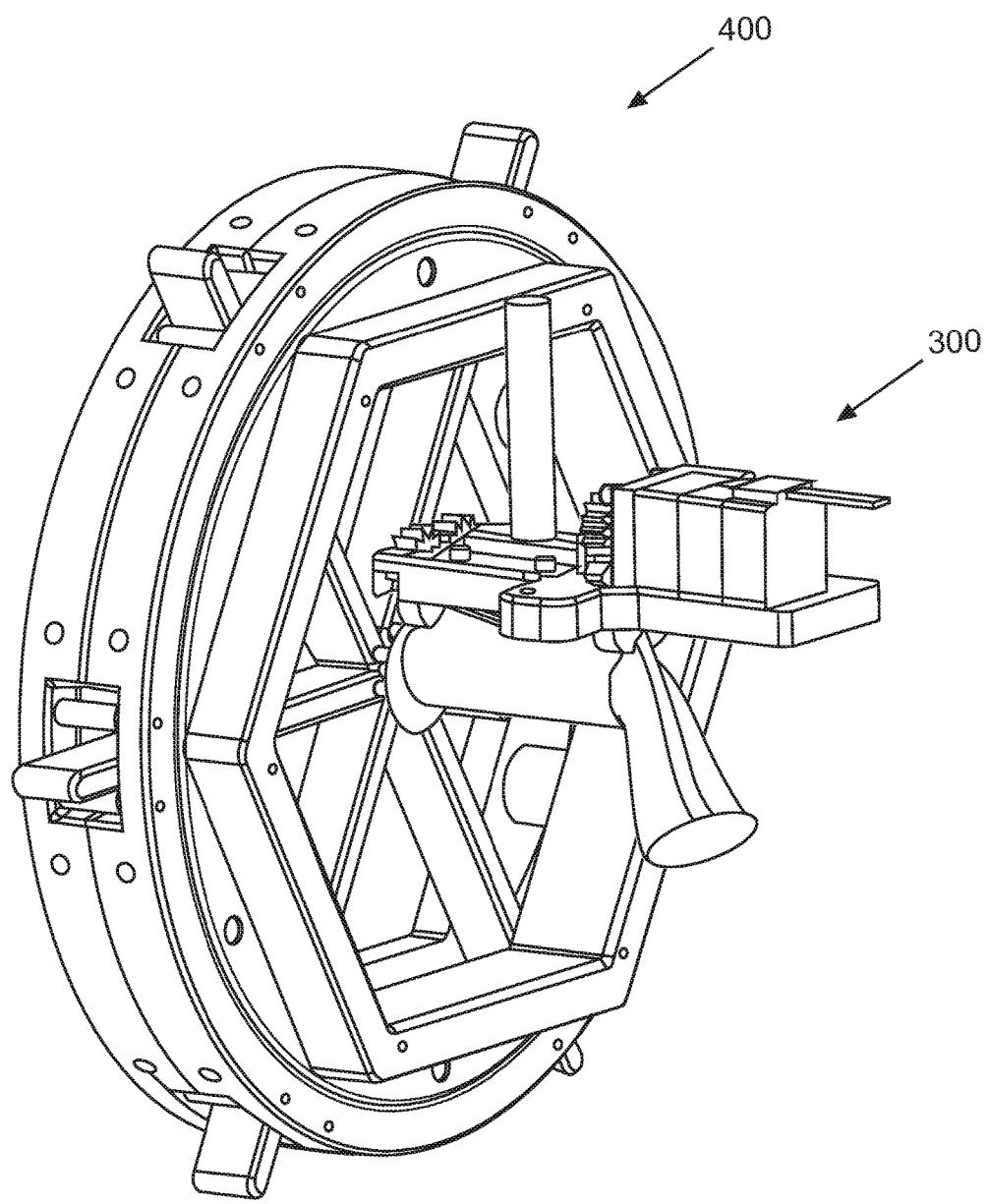

The inner end (404) of each spreading rod (402) is equipped with a grasping pin (405). FIGS. 22 and 23 depict the glove-opening device (400) wherein the grasping pins (405) are concentrated in the center of the polygonal circumferential frame (401), i.e. in closed position. The glove-opening device (400) also includes a mechanism that changes the joint angle between the spreading rods (402) and the polygonal circumferential frame (401). FIG. 24 depicts the glove-opening device (400) in partially opened position, i.e. the spreading rods (402) are rotated slightly so that their inner ends (404) are closer to the sides of the polygonal circumferential frame (401). FIG. 25 depicts the glove-opening device (400) in open position, i.e. when the spreading rods (402) are parallel and adjacent to the sides of the polygonal circumferential frame (401) and the grasping pins (405) are positioned in the angles between said sides of the polygonal circumferential frame (401).

Method of operation of the gloving apparatus (1000): The glove-lifting-and-positioning device (300) descends and picks up a glove (100) as described above. The device then ascends with the graspers (302) grasping the wrist part of the glove (100) and wherein the opening of the glove (100) is open, as depicted, for instance, in FIG. 16. When the glove opening is positioned opposite the grasping pins (405), as depicted for instance in FIG. 26, the glove-lifting-and-positioning device (300) moves horizontally until the glove opening is inserted over the grasping pins (405), as depicted for instance in FIG. 27, and at the same time the graspers (302) release the glove. At this point, the glove-opening device (400) goes from closed to open position, in other words, to a position in which the glove opening is stretched into the shape of the polygonal circumferential frame, and the glove, in fact, is sealing the opening of the glove-opening device (400). The glove-inflating device (500), which may be an air pump for instance, now creates sub-pressure within the casing (200), causing the glove to inflate. The user can now insert his or her hand into the inflated glove which, as a result of its slight inward motion, is released from the grasping pins (405), remaining on the user's hand.

A sensor that identifies full insertion of the hand into the glove controls the release of the glove by the pins (405). In addition, the gloving apparatus (1000) is equipped with several activators that activate each of the above mentioned apparatus parts, as well as sensors that enable it to operate automatically.

What is claimed is:

1. A gloving apparatus that comprises a glove box, a glove-lifting device, a glove-opening device, and a glove-inflating device; wherein the glove box is designed to contain gloves; wherein the glove-lifting device is designed to lift gloves, one at a time, from the glove box and insert the glove opening over said glove-opening device; wherein the glove-lifting device comprises a vertical rod with one or more fastening devices at the bottom end, and vertical and horizontal activators; wherein the glove-opening device has four spreading fingers, each of which can move horizontally and vertically using activators; and wherein the glove-inflating device comprises a sealing ring, an air tubule, and an activator that can move the sealing ring back and forth.

2. A gloving apparatus (1000) that comprises a casing, a glove-lifting-and-positioning device, a glove-opening device, and a glove-inflating device;

wherein the glove-lifting-and-positioning device comprises an activator, graspers, a vacuum tube, a vertical guide, and a horizontal guide; wherein the glove-lifting-and-positioning device is designed to move up and down on the vertical guide and back and forth on the horizontal guide; wherein the wrist part of the glove is held by the vacuum tube and the graspers;

wherein the glove-opening device comprises a polygonal circumferential frame and several spreading rods; whereby the outer end of each spreading rod is attached to the polygonal circumferential frame via an axial joint; and whereby the inner end of each spreading rod is equipped with a grasping pin;

wherein the glove-lifting-and-positioning device is designed to lift a glove and insert its opening over said grasping pins; wherein the glove-opening device can move from closed position to open position, causing the glove opening to stretch open and assume the shape of the polygonal circumferential frame; wherein the glove-inflating device creates sub-pressure in the casing, causing the glove to inflate; and wherein the user may insert his or her hand into the inflated glove.

* * * * *